US012636294B2

(12) United States Patent
Agarwal et al.

(10) Patent No.: US 12,636,294 B2
(45) Date of Patent: May 26, 2026

(54) COMPOSITIONS AND METHODS FOR THE TREATMENT OR PREVENTION OF TRAUMATIC BRAIN INJURY

(71) Applicant: Incannex Healthcare Limited, Norwest (AU)

(72) Inventors: Sudhanshu Agarwal, Toorak (AU); Joel Bradley Latham, North Kellyville (AU); Mark Robert Bleackley, South Morang (AU)

(73) Assignee: Incannex Healthcare Limited, Norwest (AU)

( * ) Notice: Subject to any disclaimer, the term of this patent is extended or adjusted under 35 U.S.C. 154(b) by 935 days.

(21) Appl. No.: 17/638,264

(22) PCT Filed: Oct. 2, 2020

(86) PCT No.: PCT/AU2020/051056

§ 371 (c)(1),
(2) Date: Feb. 25, 2022

(87) PCT Pub. No.: WO2021/062481

PCT Pub. Date: Apr. 8, 2021

(65) Prior Publication Data

US 2022/0288016 A1 Sep. 15, 2022

(30) Foreign Application Priority Data

Oct. 4, 2019 (AU) ................................ 2019903734

(51) Int. Cl.
*A61P 25/00* (2006.01)
*A61K 31/00* (2006.01)
*A61K 31/08* (2006.01)

(52) U.S. Cl.
CPC ............ *A61K 31/658* (2023.05); *A61K 31/08* (2013.01); *A61P 25/00* (2018.01)

(58) Field of Classification Search
CPC .................................................... A61K 31/352
See application file for complete search history.

(56) References Cited

U.S. PATENT DOCUMENTS

2017/0143664 A1 5/2017 Ankner

FOREIGN PATENT DOCUMENTS

WO WO-2009/043395 A2 4/2009
WO WO-2017/066744 A1 4/2017
WO WO-2021/062481 A1 4/2021

OTHER PUBLICATIONS

Belardo et al., "Oral Cannabidiol Prevents Allodynia and Neurological Dysfunctions in a Mouse Model of Mild Traumatic Brain Injury," Frontiers in Pharmacology, 10: Article 352 pp. 1-11 (2019).
International Search Report and Written Opinion for International Application No. PCT/AU2020/051056 dated Nov. 9, 2020.
McVige et al., "Medical Cannabis in the Treatment of Post-Traumatic Concussion (p. 3.9-027)," Neurology, 92: Supplement 15, p. 3.9-027 (2019).
Rowe et al., "Using anesthetics and analgesics in experimental traumatic brain injury," Lab Animal, 42(8): 286-291 (2013).
Benzonana et al., "Isoflurane, a Commonly Used Volatile Anesthetic, Enhances Renal Cancer Growth and Malignant Potential via the Hypoxia-inducible Factor Cellular Signaling Pathway In Vitro," Anesthesiology 119 (2013): 593-605.
Incannex Heathcare, "Impression Healthcare #ASX Announcement: Proprietary IHL-216A cannabinoid drug being assessed for #traumaticbraininjury #concussion," X, Apr. 23, 2020, retrieved from the internet: https://twitter.com/asx_ihl/status/1253121390548414465.
Incannex, "Proprietary IHL-216A for Concussion/Traumatic Brain Injury ('TBI') and CTE," Apr. 23, 2020, retrieved from https://announcements.asx.com.au/asxpdf/20200423/pdf/44h5xbzd332khz.pdf.
Statler et al., "Isoflurane exerts neuroprotective actions at or near the time of severe traumatic brain injury," Brain Research 1076.1 (2006): 216-224.
Supplementary European Search Report for EP Application No. 20870484.1 dated Sep. 21, 2023.

*Primary Examiner* — Yong S. Chong
(74) *Attorney, Agent, or Firm* — Foley Hoag LLP; Deann F. Smith; Philip S. Choi

(57) ABSTRACT

The present disclosure relates to methods and compositions comprising cannabidiol (CBD) and a volatile anaesthetic, particularly isoflurane, useful for treating or preventing traumatic brain injury (TBI).

21 Claims, No Drawings

COMPOSITIONS AND METHODS FOR THE TREATMENT OR PREVENTION OF TRAUMATIC BRAIN INJURY

FIELD

The present disclosure relates generally to compositions and methods useful for treating or preventing traumatic brain injury (TBI).

RELATED APPLICATIONS

This application is the U.S. national phase of International Patent Application No. PCT/AU2020/051056 filed on 2 Oct. 2020, which claims the benefit of priority from Australian Provisional Patent Application Serial No. 2019903734 filed on 4 Oct. 2019, the entire contents of each of said applications are hereby incorporated in their entirety by this reference.

BACKGROUND

Traumatic brain injury (TBI) results from damage to the brain structure and function caused by an acute external physical force. The short-term effects of acute brain injury including subdural haematoma and catastrophic brain injury may lead to death, whereas mild TBI, or concussion, causes functional disturbance and axonal injury rather than gross structural brain damage. While the extent of TBI can vary significantly, the mechanism by which TBI occurs is determined by the nature of the primary insult (i.e., primary damage, mechanical damage) occurring at the moment of impact, together with the secondary insult (secondary damage, delayed non-mechanical damage), which represent consecutive pathological processes initiated at the moment of injury with delayed clinical presentation.

TBI is recognised as a leading cause of morbidity and mortality worldwide. TBI occur as result of motor vehicle accidents, falls, assaults and in individuals who participate in contact sports such as boxing, mixed martial arts, kick boxing, football, rugby, etc. Acute brain injury in sports-related trauma may lead to concussion, sub-concussion, haemorrhage or other structural brain damages. The chronic consequence of TBI is chronic traumatic encephalopathy (CTE), a neurodegenerative condition also commonly referred to as “punch-drunk” syndrome. Despite this, there are currently no effective pharmacological approaches for the treatment or prevention of TBI. In fact, clinical management of TBI is primarily limited to surgical intervention by decompressive craniotomy, which involves the removal of skull segments to reduce intracranial pressure. Therefore, there remains an urgent need for the development of pharmacological approaches for the treatment or prevention of TBI.

SUMMARY

In an aspect of the present disclosure, there is provided a method for the treatment or prevention of traumatic brain injury (TBI) comprising administering to a subject in need thereof a loading dose comprising an effective amount of cannabidiol (CBD), or a pharmaceutically acceptable salt thereof, and a volatile anaesthetic, or a pharmaceutically acceptable salt thereof.

In another aspect of the present disclosure, there is provided a composition comprising CBD, or a pharmaceutically acceptable salt thereof, and a volatile anaesthetic, or a pharmaceutically acceptable salt thereof.

In another aspect of the present disclosure, there is provided a composition comprising CBD, or a pharmaceutically acceptable salt thereof, and a volatile anaesthetic, or a pharmaceutically acceptable salt thereof, for use in the treatment or prevention of TBI.

In another aspect of the present disclosure, there is provided a method for the treatment or prevention of TBI comprising administering to a subject in need thereof an effective amount of the composition comprising CBD, or a pharmaceutically acceptable salt thereof, and a volatile anaesthetic, or a pharmaceutically acceptable salt thereof.

In another aspect of the present disclosure, there is provided a use of CBD, or a pharmaceutically acceptable salt thereof, and a volatile anaesthetic, or a pharmaceutically acceptable salt thereof, in the manufacture of a medicament for the treatment or prevention of TBI.

DETAILED DESCRIPTION

Unless defined otherwise, all technical and scientific terms used herein have the same meaning as commonly understood by those of ordinary skill in the art to which the disclosure belongs. Any materials and method similar or equivalent to those described herein can be used to practice the present invention.

Throughout this specification, unless the context requires otherwise, the word “comprise”, or variations such as “comprises” or “comprising”, will be understood to imply the inclusion of the stated element or integer or group of elements or integers but not the exclusion of any other element or integer or group of elements or integers.

The phrase “consisting of” means including, and limited to, whatever follows the phrase “consisting of”. Thus, the phrase “consisting of” indicates that the listed elements are required or mandatory, and that no other elements may be present. The phrase “consisting essentially of” means including any elements listed after the phrase, and limited to other elements that do not interfere with or contribute to the activity or action specified in the disclosure for the listed elements. Thus, the phrase “consisting essentially of” indicates that the listed elements are required or mandatory, but that other elements are optional and may or may not be present depending upon whether or not they affect the activity or action of the listed elements.

As used herein the singular forms “a”, “an” and “the” include plural aspects unless the context clearly dictates otherwise. Thus, for example, reference to “a compound” includes a single compound, as well as two or more compounds; reference to “an agent” includes one agent, as well as two or more agents; and so forth.

The term “about” will be understood by persons skilled in the art and will vary to some extent depending on the context in which it is used. If there are uses of the term that are not clear to persons skilled in the art, given the context which it is used, “about” will mean up to plus or minus 10% of the particular term.

Treatment of Traumatic Brain Injury (TBI)

The present disclosure is predicated, at least in part, on the inventor’s surprising finding that the administration of cannabidiol (CBD) and a volatile anaesthetic, e.g., isoflurane, can synergise to protect the brain from secondary immune-mediated damage associated with traumatic brain injury (TBI), thereby providing a neuroprotective effect following head injury. This finding has been reduced to practice in a method for the treatment or prevention of TBI.

Thus, in an aspect of the present disclosure, there is provided a method of treating or preventing TBI comprising administering to a subject in need thereof a loading dose comprising an effective amount of CBD, or a pharmaceutically acceptable salt thereof, and a volatile anaesthetic, or a pharmaceutically acceptable salt thereof.

"Cannabidiol" or "CBD" is a cannabinoid produced by plants of the genus *Cannabis*. CBD has antagonist activity on agonists of the CB1 and CB2 receptors.

CBD is synthesised in *Cannabis* plants as cannabidiolic acid (CBDA), which decarboxylates to CBD (Table 1). While some decarboxylation may occur in the plant, decarboxylation typically occurs post-harvest and is increased by exposing plant material to heat (Sanchez and Verpoote, 2008, *Plant and Cell Physiology,* 49(12): 1767-82). Decarboxylation is usually achieved by drying and/or heating the plant material. Persons skilled in the art would be familiar with methods by which decarboxylation of CBDA can be promoted, illustrative examples of which include air-drying, combustion, vaporisation, curing, heating and baking. The decarboxylated CBD will typically bind to and/or stimulate, directly or indirectly, cannabinoid receptors including CB1 and/or CB2. Accordingly, CBD displays activity as a ligand of cannabinoid receptors such as CB1 and CB2 and has been suggested to act as an inverse agonist of these receptors.

material include the methods described in U.S. patent Ser. No. 10/189,762 and WO 2004/016277.

In a preferred embodiment, the CBD described herein is a synthetic compound. Synthesised CBD is particularly useful for pharmaceutical development it is largely free from contaminants. A large number of synthetic cannabinoids displaying analgesic and/or other beneficial properties have been described in, e.g., Rahn and Hohmann, 2009*, Neurotherapeutics* 6:713-37.

The term "loading dose" as used herein refers to an initial or first dose of an agent or combination of agents, e.g., CBD and/or a volatile anaesthetic.

As used herein, the terms "volatile anaesthetic" or "VA" refer to a class of anaesthetic agents that are liquid at room temperature, but evaporate easily for administration by inhalation. Volatile anaesthetics raise the excitatory threshold of neurons and, therefore, may reduce the degree of neuro excitation post-head injury. Suitable volatile anaesthetics will be known to persons skilled in the art, illustrative examples of which include methoxyflurane, halothane, enflurane, isoflurane, sevoflurane and desflurane.

In an embodiment, the volatile anaesthetic is a halogenated volatile anaesthetic, or a pharmaceutically acceptable salt thereof. In another embodiment, the volatile anaesthetic is an organofluorine compound. In an embodiment, the

TABLE 1

Cannabidiol and related cannabinoids

| Name | Structure | Chemical properties/ $[M + H]^+$ ESI MS |
|---|---|---|
| cannabidiol (CBD) | 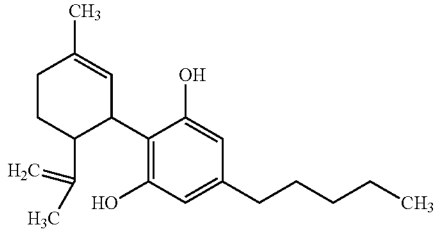 [SMILES: C=C(C)C1CCC(C)=CC1c1c(O)cc(CCCCC)cc1O] | decarboxylation product of CBDA m/z 315.2319 |
| cannabidiolic acid (CBDA) | 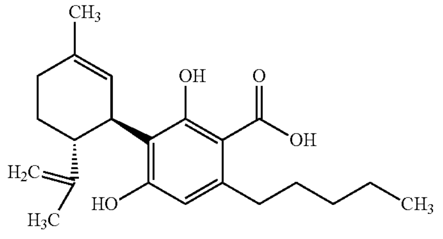 [SMILES: C=C(C)[C@@H]1CCC(C)=C[C@H]1c1c(O)cc(CCCCC)c(C(=O)O)c1O] | m/z 359.2217 |
| cannabigerolic acid (CBGA) | 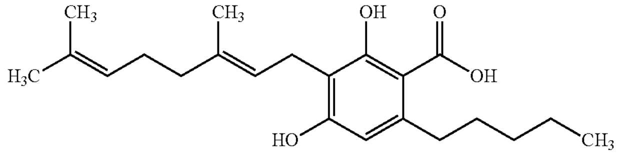 [SMILES: CCCCCc1cc(O)c(C/C=C(\C)CCC=C(C)C)c(O)c1C(=O)O] | m/z 361.2373 |

CBD may be extracted from any suitable plant parts including leaves, flowers or stems and may be produced by any suitable means known to those skilled in the art. For example, CBD extracts may be produced by extraction with supercritical or subcritical $CO_2$, or by volatilisation of plant material with a heated gas. Illustrative examples of methods used the extract CBD and other cannabinoids from plant organofluorine compound is methoxyflurane or isoflurane. In a preferred embodiment, the organofluorine compound is isoflurane.

The terms "traumatic brain injury" or "TBI" will be understood by persons skilled in the art as meaning an injury to the brain caused by an external force. Common causes include falls, car accidents, assault or being struck by objects during sport. The outcome of a head injury sustained by a subject is determined by two substantially different mechanisms: (i) the primary insult (i.e., primary damage, mechanical damage) occurring at the time of impact; and (ii) the secondary insult (i.e., secondary damage, delayed non-mechanical damage), which represents the consecutive pathological processes initiated at the time of impact with delayed clinical presentation. The primary insult is characterised by direct tissue damage and impaired regulation of cerebral blood flow (CBF) and metabolism. This ischaemia-like pattern leads to accumulation of lactic acid due to anaerobic glycolysis, increased membrane permeability, and consecutive oedema formation. The secondary insult broadly encompasses a range of different pathophysiological outcomes, which may include, for example, terminal membrane depolarisation, releases of excitatory neurotransmitters (e.g., glutamate, aspartate), $Ca^{2+}$- and/or $Na^{2+}$-mediated catabolic intracellular processes, and activation of immunomodulators (e.g., cytokines, prostaglandins, free radicals and complement). Together, these events lead to membrane degradation of vascular and cellular structure and neuronal cell death (e.g., necrotic or apoptotic).

In an embodiment, the method described herein may be useful in reducing or preventing neuronal cell death during the secondary insult of TBI. In particular embodiments, when a loading dose comprising an effective amount of CBD, or a pharmaceutically acceptable salt thereof, and a volatile anaesthetic, or a pharmaceutically acceptable salt thereof, is administered to a subject from about 10 minutes to about 24 hours after a head injury (i.e., the primary insult) has occurred, neuronal excitation and/or inflammation may be reduced, which results in a corresponding reduction in cerebral oxygen consumption and CBF thereby providing neuroprotection.

TBI is classified according to its severity: mild, moderate or severe. Classification may be clinically determined based on the Glasgow Coma Scale (GCS) (Ghelichkhani et al., 2018, *Emergency* (*Tehran*), 6(1): e42), which assesses motor, verbal and eye-opening responses. A subject with mild TBI will have a GCS of between 13 and 15; a subject with moderate TBI will have a GCS of between 9 and 12; and a subject with severe TBI will have a GCS less than 9. In the absence of a clinical assessment, TBI is considered moderate to severe if there is a loss of consciousness that is longer than 30 minutes and amnesia that lasts for more than 24 hours. If these conditions are not met, TBI is classified as mild. Concussion in the absence of other symptoms is typically classified as a mild TBI.

In an embodiment, the TBI is mild to severe TBI. In another embodiment, the TBI is moderate to severe TBI.

In an embodiment, the subject has acquired TBI while participating in a contact sport.

The term "subject" as used herein refers to any mammal, including livestock and other farm animals (such as cattle, goats, sheep, horses, pigs and chickens), performance animals (such as racehorses), companion animals (such as cats and dogs), laboratory test animals and humans. In an embodiment, the subject is a human. In an embodiment, the subject is an adult. In another embodiment, the subject is a child.

As used herein, the term "effective amount" typically refers to an amount of CBD and a volatile anaesthetic, including combinations thereof, that is sufficient to affect one or more beneficial or desired therapeutic outcomes (e.g., reduction in neuronal excitation, reduction in neuronal inflammation, reduction in CBF, reduction in cerebral oxygen consumption, improved recovery from neurocognitive deficit, improved recovery from motor function deficit). Said beneficial or desired therapeutic outcomes may be measured using clinical techniques known in the art, illustrative examples of which include the measurement of cerebral haemoglobin flow (CHbF) and cerebral venous oxyhemoglobin saturation ($CS_{VO2}$) using near infrared spectroscopy, magnetic resonance imaging (MRI) estimation of global brain oxygen consumption rate as described by Jain et al. (2010, *Journal of Cerebral Blood Flow & Metabolism,* 30(9): 1598-1607), quantification of the presence of inflammatory mediators (e.g., Interleukin-1, TNF, TGF-β, etc.), immunohistochemistry for markers of microglial activation (i.e., IBA1), astrocytic response (i.e., GFAP) and neuronal loss (i.e., NeuN or Flurojade), electroencephalography (EEG), and neurocognitive test battery (e.g. ImPACT, Cogstate, etc.) An "effective amount" can be provided in one or more administrations. The exact amount required may vary depending on factors such as the nature and severity of the TBI to be treated, the age and general health of the subject, and the form in which the active agents are to be administered.

The terms "treat", "treating", "treatment" and the like are used interchangeably herein to mean relieving, reducing, alleviating, ameliorating or otherwise inhibiting the severity and/or progression of TBI, or a symptom thereof, in a subject. It is to be understood that the terms "treat", "treating", "treatment" and the like, as used herein, do not imply that a subject is treated until clinical symptoms of TBI have been eliminated or are no longer evident (e.g., neuronal excitation, neuronal inflammation, CBF, cerebral oxygen consumption). Said treatment may also reduce the severity of TBI by preventing intracerebral neuronal damage with clinical sequelae.

The terms "prevent", "preventing", "prevention" and the like are used interchangeably herein to mean inhibit, hinder, retard, reduce or otherwise delay the development of TBI and/or progression of TBI, or a symptom thereof, in a subject. In the context of the present disclosure, the term "prevent" and variations thereof does not necessarily imply the complete prevention of the specified event. Rather, the prevention may be to an extent, and/or for a time, sufficient to produce the desired effect. Prevention may be inhibition, retardation, reduction or otherwise hindrance of the event, activity or function. Such preventative effects may be in magnitude and/or be temporal in nature.

In accordance with the methods disclosed herein, the CBD and volatile anaesthetic may be administered sequentially or simultaneously, and as part of the same loading dose or as part of separate loading doses (e.g., a first loading dose comprising the CBD and a second loading dose comprising the volatile anaesthetic).

In an embodiment, the loading dose is administered from about 10 minutes to about 24 hours after a head injury has occurred (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes; or 1, 2, 3, 4, 5, 6, 7, 8, 9, 10, 11, 12, 13, 14, 15, 16, 17, 18, 19, 20, 21, 22, 23, 24 hours). Thus, in an embodiment, the loading dose is administered about 10 minutes, preferably about 11 minutes, preferably about 12 minutes, preferably about 13 minutes, preferably about 14 minutes, preferably about 15 minutes, preferably about 16 minutes, preferably about 17 minutes, preferably about 18 minutes, preferably about 19 minutes, preferably about 20 minutes, preferably about 21 minutes, preferably about 22 minutes, preferably about 23 minutes, preferably about 24 minutes, preferably about 25 minutes, preferably about 26 minutes, preferably about 27 minutes, preferably about 28 minutes, preferably about 29 minutes, preferably about 30 minutes, preferably about 31 minutes, preferably about 32 minutes, preferably about 33 minutes, preferably about 34 minutes, preferably about 35 minutes, preferably about 36 minutes, preferably about 37 minutes, preferably about 38 minutes, preferably about 39 minutes, preferably about 40 minutes, preferably about 41 minutes, preferably about 42 minutes, preferably about 43, preferably about 44, preferably about 45, preferably about 46, preferably about 47 minutes, preferably about 48 minutes, preferably about 49 minutes, preferably about 50 minutes, preferably about 51 minutes, preferably about 52 minutes, preferably about 53 minutes, preferably about 54 minutes, preferably about 55 minutes, preferably about 56 minutes, preferably about 57 minutes, preferably about 58 minutes, preferably about 59 minutes, or more preferably about 60 minutes after a head injury has occurred. In another embodiment, the loading dose is administered about 1 hour, preferably about 2 hours, preferably about 3 hours, preferably about 4 hours, preferably about 5 hours, preferably about 6 hours, preferably about 7 hours, preferably about 8 hours, preferably about 9 hours, preferably about 10 hours, preferably about 11 hours, preferably about 12 hours, preferably about 13 hours, preferably about 14 hours, preferably about 15 hours, preferably about 16 hours, preferably about 17 hours, preferably about 18 hours, preferably about 19 hours, preferably about 20 hours, preferably about 21 hours, preferably about 22 hours, preferably about 23 hours, or more preferably about 24 hours after a head injury has occurred.

As noted elsewhere herein, the CBD and the volatile anaesthetic may be formulated in the same loading dose (e.g., for simultaneous administration) or they may be formulated as different loading doses for sequential administration. By "sequential" administration is meant there is an interval between the administration of the CBD and the volatile anaesthetic. The interval between sequential administrations may be seconds, minutes, hours or days. In an embodiment, the interval between sequential administrations of the CBD and the volatile anaesthetic is from about 30 minutes to about 2 hours. Sequential administration may be in any order.

Where the loading dose of the CBD and the volatile anaesthetic are administered sequentially, the CBD may be administered first, and the volatile anaesthetic administered thereafter, and vice versa. In certain embodiments, the loading dose of the CBD may be administered to the subject from about 15 minutes to about 30 minutes after a head injury has occurred, and the loading dose of the volatile anaesthetic may be administered to the subject from about 1 hour to about 2 hours after the head injury has occurred.

In an embodiment, the loading dose of the CBD and the volatile anaesthetic may be co-administered with one or more other agents suitable for the amelioration of symptoms associated with TBI, illustrative examples of which include anti-anxiety agents, anti-coagulants, anti-convulsants, anti-depressants, muscle relaxants and stimulants.

In an embodiment, the method further comprises the administration of one or more cannabinoids selected from the group consisting of cannabigerol (CBG), cannabinol (CBN), cannabinodiol (CBDL), cannabichromene (CBC) and delta-9-tetrahydrocannabinol (THC).

In accordance with the methods disclosed herein, the volatile anaesthetic is administered to the subject by inhalation. For inhalation, the volatile anaesthetic can be administered using any suitable delivery system, illustrative examples of which include liquid delivery systems, metered dose inhaler (MDI) systems, nebulisers, propellant systems, and combinations thereof.

In an embodiment, the volatile anaesthetic is administered in vapour form. For vaporised administration, the active agents can be formulated as a liquid comprising suitable carriers, diluents and excipients to stabilise the active agents in the composition, including emulsifiers, flavour enhancers and antioxidant preservatives. Suitable protocols for the administration volatile anaesthetics would be known to persons skilled in the art, illustrative examples of which include the methods described by Solowij et al. (2014, *BMC Pharmacology and Toxicology,* 15), Blair and Frampton (2016, *Clinical Drug Investigation,* 36(12): 1067-1073) and in WO 2016001922.

In some embodiments, periodic re-administration of the active agents (e.g., either sequentially or co-administered) may be required to achieve a desirable therapeutic effect. The exact amounts and rates of administration of the CBD and the volatile anaesthetic will depend on a number of factors, examples of which are described elsewhere herein, such as the subject's age, body weight, general health, sex and dietary requirements, as well as any drugs or agents used in combination or coincidental with the administration of the composition. Where multiple divided doses are required, these may be administered hourly, daily, weekly, monthly or at other suitable time intervals or the dose may be proportionally reduced as indicated by the exigencies of the situation.

The term "maintenance dose" as used herein refers to one or more subsequent doses of CBD and/or the volatile anaesthetic after the initial loading dose.

In an embodiment disclosed herein, the subject is administered one or more maintenance dose(s) of the CBD, wherein the maintenance dose of the CBD is administered subsequent to the administration of the loading dose.

The number and frequency of the administration of the maintenance dose(s) of the CBD to be administered to the subject will depend on a number of factors, examples of which are described elsewhere herein, such as the subject's age, body weight, general health, sex and dietary requirements, as well as the subject's responsiveness to the loading dose.

In an embodiment, the maintenance dose is administered at least one day after the administration of the loading dose.

In an embodiment, the maintenance dose is administered daily.

In an embodiment, the maintenance dose is administered over three consecutive days after the administration of the loading dose. In another embodiment, the maintenance dose is administered over five consecutive days after the administration of the loading dose. In yet another embodiment, the maintenance dose is administered over six consecutive days after the administration of the loading dose.

In another embodiment, the maintenance dose is administered chronically after the administration of the loading dose.

In an embodiment, the loading dose comprises from about 0.1 mg to about 1000 mg of the CBD (e.g., 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, or 1000 mg). Thus, in an embodiment, the loading dose comprises about 0.1 mg, preferably about 0.2 mg, preferably about 0.3 mg, preferably about 0.4 mg, preferably about 0.5 mg, preferably about 0.6 mg, preferably about 0.7 mg, preferably about 0.8 mg, preferably about 0.9 mg, preferably about 1 mg, preferably about 2 mg, preferably about 3 mg, preferably about 4 mg, preferably about 5 mg, preferably about 6 mg, preferably about 7 mg, preferably about 8 mg, preferably about 9 mg, preferably about 10 mg, preferably about 20 mg, preferably about 30 mg, preferably about 40 mg, preferably about 50 mg, preferably about 60 mg, preferably about 70 mg, preferably about 80 mg, preferably about 90 mg, preferably about 100 mg, preferably about 110 mg, preferably about 120 mg, preferably about 130 mg, preferably about 140 mg, preferably about 150 mg, preferably about 160 mg, preferably about 170 mg, preferably about 180 mg, preferably about 190 mg, preferably about 200 mg, preferably about 210 mg, preferably about 220 mg, preferably about 230 mg, preferably about 240 mg, preferably about 250 mg, preferably about 260 mg, preferably about 270 mg, preferably about 280 mg, preferably about 290 mg, preferably about 300 mg, preferably about 310 mg, preferably about 320 mg, preferably about 330 mg, preferably about 340 mg, preferably about 350 mg, preferably about 360 mg, preferably about 370 mg, preferably about 380 mg, preferably about 390 mg, preferably about 400 mg, preferably about 410 mg, preferably about 420 mg, preferably about 430 mg, preferably about 440 mg, preferably about 450 mg, preferably about 460 mg, preferably about 470 mg, preferably about 480 mg, preferably about 490 mg, preferably about 500 mg, preferably about 510 mg, preferably about 520 mg, preferably about 530 mg, preferably about 540 mg, preferably about 550 mg, preferably about 560 mg, preferably about 570 mg, preferably about 580 mg, preferably about 590 mg, preferably about 700 mg, preferably about 710 mg, preferably about 720 mg, preferably about 730 mg, preferably about 740 mg, preferably about 750 mg, preferably about 760 mg, preferably about 770 mg, preferably about 780 mg, preferably about 790 mg, preferably about 800 mg, preferably about 810 mg, preferably about 820 mg, preferably about 830 mg, preferably about 840 mg, preferably about 850 mg, preferably about 860 mg, preferably about 870 mg, preferably about 880 mg, preferably about 890 mg, preferably about 900 mg, preferably about 910 mg, preferably about 920 mg, preferably about 930 mg, preferably about 940 mg, preferably about 950 mg, preferably about 960 mg, preferably about 970 mg, preferably about 980 mg, preferably about 990 mg, or more preferably about 1000 mg of the CBD.

In an embodiment, the loading dose comprises an amount of the volatile anaesthetic effective to target a Minimum Alveolar Concentration (MAC) of at least 0.01 (e.g., 0.01, 0.02, 0.03, and so on).

In an embodiment, the loading dose comprises an amount of the volatile anaesthetic effective to target a MAC of from about 0.01 to about 10 (e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10). Thus, in an embodiment, the loading dose comprises an amount of the volatile anaesthetic effective to target a MAC of about 0.01, preferably about 0.02, preferably about 0.03, preferably about 0.04, preferably about 0.05, preferably about 0.06, preferably about 0.07, preferably about 0.08, preferably about 0.09, preferably about 0.1, preferably about 0.2, preferably about 0.3, preferably about 0.4, preferably about 0.5, preferably about 0.6, preferably about 0.7, preferably about 0.8, preferably about 0.9, preferably about 1, preferably about 1.5, preferably about 2, preferably about 2.5, preferably about 3, preferably about 3.5, preferably about 4, preferably about 4.5, preferably about 5, preferably about 5.5, preferably about 6, preferably about 6.5, preferably about 7, preferably about 7.5, preferably about 8, preferably about 8.5, preferably about 9, preferably about 9.5 or more preferably about 10.

In an embodiment, the volatile anaesthetic is methoxyflurane, wherein the loading dose comprises an amount of methoxyflurane effective to target a MAC of 0.3.

In another embodiment, the volatile anaesthetic is isoflurane, wherein the loading dose comprises an amount of isoflurane effective to target a MAC of 1.5.

In an embodiment, the maintenance dose comprises from about 0.1 mg to about 1000 mg of the CBD (e.g., 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, or 1000 mg). Thus, in an embodiment, the maintenance dose comprises about 0.1 mg, preferably about 0.2 mg, preferably about 0.3 mg, preferably about 0.4 mg, preferably about 0.5 mg, preferably about 0.6 mg, preferably about 0.7 mg, preferably about 0.8 mg, preferably about 0.9 mg, preferably about 1 mg, preferably about 2 mg, preferably about 3 mg, preferably about 4 mg, preferably about 5 mg, preferably about 6 mg, preferably about 7 mg, preferably about 8 mg, preferably about 9 mg, preferably about 10 mg, preferably about 20 mg, preferably about 30 mg, preferably about 40 mg, preferably about 50 mg, preferably about 60 mg, preferably about 70 mg, preferably about 80 mg, preferably about 90 mg, preferably about 100 mg, preferably about 110 mg, preferably about 120 mg, preferably about 130 mg, preferably about 140 mg, preferably about 150 mg, preferably about 160 mg, preferably about 170 mg, preferably about 180 mg, preferably about 190 mg, preferably about 200 mg, preferably about 210 mg, preferably about 220 mg, preferably about 230 mg, preferably about 240 mg, preferably about 250 mg, preferably about 260 mg, preferably about 270 mg, preferably about 280 mg, preferably about 290 mg, preferably about 300 mg, preferably about 310 mg, preferably about 320 mg, preferably about 330 mg, preferably about 340 mg, preferably about 350 mg, preferably about 360 mg, preferably about 370 mg, preferably about 380 mg, preferably about 390 mg, preferably about 400 mg, preferably about 410 mg, preferably about 420 mg, preferably about 430 mg, preferably about 440 mg, preferably about 450 mg, preferably about 460 mg, preferably about 470 mg, preferably about 480 mg, preferably about 490 mg, preferably about 500 mg, preferably about 510 mg, preferably about 520 mg, preferably about 530 mg, preferably about 540 mg, preferably about 550 mg, preferably about 560 mg, preferably about 570 mg, preferably about 580 mg, preferably about 590 mg, preferably about 700 mg, preferably about 710 mg, preferably about 720 mg, preferably about 730 mg, preferably about 740 mg, preferably about 750 mg, preferably about 760 mg, preferably about 770 mg, preferably about 780 mg, preferably about 790 mg, preferably about 800 mg, preferably about 810 mg, preferably about 820 mg, preferably about 830 mg, preferably about 840 mg, preferably about 850 mg, preferably about 860 mg, preferably about 870 mg, preferably about 880 mg, preferably about 890 mg, preferably about 900 mg, preferably about 910 mg, preferably about 920 mg, preferably about 930 mg, preferably about 940 mg, preferably about 950 mg, preferably about 960 mg, preferably about 970 mg, preferably about 980 mg, preferably about 990 mg, or more preferably about 1000 mg of the CBD.

In an embodiment, the loading dose of the CBD is administered to the subject by a method selected from the group consisting of inhalation, oral administration, nasal administration and parenteral administration (e.g., injection).

In an embodiment, the loading dose of the CBD is administered to the subject by parenteral administration.

In an embodiment, the loading dose of the CBD is administered to the subject by inhalation.

In an embodiment, the maintenance dose of the CBD is administered to the subject by a method selected from the group consisting of inhalation, oral administration, nasal administration and parenteral administration (e.g., injection).

In an embodiment, the maintenance dose of the CBD is administered to the subject by parenteral administration.

In an embodiment, the maintenance dose of the CBD is administered to the subject by inhalation. In another embodiment, the maintenance dose of the CBD is administered to the subject orally.

Those skilled in the art will appreciate that the method for the administration of the loading and maintenance dose need not be the same. Thus, the methods of the present disclosure contemplate the administration of, for example, the loading dose of the CBD by parenteral administration and the maintenance dose of the CBD by oral administration.

In other embodiments disclosed herein, the CBD and the volatile anaesthetic are formulated as separate unit dosage forms for administration. The unit dosage form may be suitable for an inhaler, a nebuliser, an atomiser, an MDI or a vaporiser. In an embodiment, the unit dosage form suitable for a vaporiser. Those skilled in the art will appreciate that unit dosage forms comprising the CBD and/or the volatile anaesthetic need not be of the same type. Thus, methods of the present disclosure contemplate the administration of, for example, the CBD by vaporiser and the volatile anaesthetic by a MDI.

Compositions

Also provided herein are compositions comprising CBD, or a pharmaceutically acceptable salt thereof, and a volatile anaesthetic, or a pharmaceutically acceptable salt thereof.

In an embodiment, the CBD is a synthetic compound.

In an embodiment, the volatile anaesthetic is an organofluorine compound.

In an embodiment, the organofluorine compound is isoflurane or methoxyflurane. In another embodiment, the organofluorine compound is isoflurane.

For inhalation, the compositions can be formulated for administration by any suitable delivery system known to persons skilled in the art, illustrative examples of which include dry powder aerosols, liquid delivery systems, MDI, nebulisers, propellant systems, and the like. In an embodiment, the composition is formulated for administration in a vapour form.

In an embodiment, the composition comprises a concentration of CBD in a total amount by weight of from about 0.1% to about 90%, preferably from about 0.1% to about 89%, preferably from about 0.1% to about 88%, preferably from about 0.1% to about 87%, preferably from about 0.1% to about 86%, preferably from about 0.1% to about 85%, preferably from about 0.1% to about 84%, preferably from about 0.1% to about 83%, preferably from about 0.1% to about 82%, preferably from about 0.1% to about 81%, preferably from about 0.1% to about 80%, preferably from about 0.1% to about 79%, preferably from about 0.1% to about 78%, preferably from about 0.1% to about 77%, preferably from about 0.1% to about 76%, preferably from about 0.1% to about 75%, preferably from about 0.1% to about 74%, preferably from about 0.1% to about 73%, preferably from about 0.1% to about 72%, preferably from about 0.1% to about 71%, preferably from about 0.1% to about 70%, preferably from about 0.1% to about 69%, preferably from about 0.1% to about 68%, preferably from about 0.1% to about 67%, preferably from about 0.1% to about 66%, preferably from about 0.1% to about 65%, preferably from about 0.1% to about 64%, preferably from about 0.1% to about 63%, preferably from about 0.1% to about 62%, preferably from about 0.1% to about 61%, preferably from about 0.1% to about 60%, preferably from about 0.1% to about 59%, preferably from about 0.1% to about 58%, preferably from about 0.1% to about 57%, preferably from about 0.1% to about 56%, preferably from about 0.1% to about 55%, preferably from about 0.1% to about 54%, preferably from about 0.1% to about 53%, preferably from about 0.1% to about 52%, preferably from about 0.1% to about 51%, preferably from about 0.1% to about 50%, preferably from about 0.1% to about 49%, preferably from about 0.1% to about 48%, preferably from about 0.1% to about 47%, preferably from about 0.1% to about 46%, preferably from about 0.1% to about 45%, preferably from about 0.1% to about 44%, preferably from about 0.1% to about 43%, preferably from about 0.1% to about 42%, preferably from about 0.1% to about 41%, preferably from about 0.1% to about 40%, preferably from about 0.1% to about 39%, preferably from about 0.1% to about 38%, preferably from about 0.1% to about 37%, preferably from about 0.1% to about 36%, preferably from about 0.1% to about 35%, preferably from about 0.1% to about 34%, preferably from about 0.1% to about 33%, preferably from about 0.1% to about 32%, preferably from about 0.1% to about 31%, preferably from about 0.1% to about 30%, preferably from about 0.1% to about 29%, preferably from about 0.1% to about 28%, preferably from about 0.1% to about 27%, preferably from about 0.1% to about 26%, preferably from about 0.1% to about 25%, preferably from about 0.1% to about 24%, preferably from about 0.1% to about 23%, preferably from about 0.1% to about 22%, preferably from about 0.1% to about 21%, preferably from about 0.1% to about 20%, preferably from about 0.1% to about 19%, preferably from about 0.1% to about 18%, preferably from about 0.1% to about 17%, preferably from about 0.1% to about 16%, preferably from about 0.1% to about 15%, preferably from about 0.1% to about 14%, preferably from about 0.1% to about 13%, preferably from about 0.1% to about 12%, preferably from about 0.1% to about 11%, preferably from about 0.1% to about 10%, preferably from about 0.1% to about 9%, preferably from about 0.1% to about 8%, preferably from about 0.1% to about 7%, preferably from about 0.1% to about 6%, preferably from about 0.1% to about 5%, preferably from about 0.1% to about 4%, preferably from about 0.1% to about 3%, preferably from about 0.1% to about 2%, or preferably from about 0.1% to about 1%.

In an embodiment, the composition is formulated for administration of from about 0.1 mg to about 1000 mg (e.g., 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, or 1000 mg) of the CBD in a single dose. Thus, in an embodiment, the composition is formulated for administration about 0.1 mg, preferably about 0.2 mg, preferably about 0.3 mg, preferably about 0.4 mg, preferably about 0.5 mg, preferably about 0.6 mg, preferably about 0.7 mg, preferably about 0.8 mg, preferably about 0.9 mg, preferably about 1 mg, preferably about 2 mg, preferably about 3 mg, preferably about 4 mg, preferably about 5 mg, preferably about 6 mg, preferably about 7 mg, preferably about 8 mg, preferably about 9 mg, preferably about 10 mg, preferably about 20 mg, preferably about 30 mg, preferably about 40 mg, preferably about 50 mg, preferably about 60 mg, preferably about 70 mg, preferably about 80 mg, preferably about 90 mg, preferably about 100 mg, preferably about 110 mg, preferably about 120 mg, preferably about 130 mg, preferably about 140 mg, preferably about 150 mg, preferably about 160 mg, preferably about 170 mg, preferably about 180 mg, preferably about 190 mg, preferably about 200 mg, preferably about 210 mg, preferably about 220 mg, preferably about 230 mg, preferably about 240 mg, preferably about 250 mg, preferably about 260 mg, preferably about 270 mg, preferably about 280 mg, preferably about 290 mg, preferably about 300 mg, preferably about 310 mg, preferably about 320 mg, preferably about 330 mg, preferably about 340 mg, preferably about 350 mg, preferably about 360 mg, preferably about 370 mg, preferably about 380 mg, preferably about 390 mg, preferably about 400 mg, preferably about 410 mg, preferably about 420 mg, preferably about 430 mg, preferably about 440 mg, preferably about 450 mg, preferably about 460 mg, preferably about 470 mg, preferably about 480 mg, preferably about 490 mg, preferably about 500 mg, preferably about 510 mg, preferably about 520 mg, preferably about 530 mg, preferably about 540 mg, preferably about 550 mg, preferably about 560 mg, preferably about 570 mg, preferably about 580 mg, preferably about 590 mg, preferably about 700 mg, preferably about 710 mg, preferably about 720 mg, preferably about 730 mg, preferably about 740 mg, preferably about 750 mg, preferably about 760 mg, preferably about 770 mg, preferably about 780 mg, preferably about 790 mg, preferably about 800 mg, preferably about 810 mg, preferably about 820 mg, preferably about 830 mg, preferably about 840 mg, preferably about 850 mg, preferably about 860 mg, preferably about 870 mg, preferably about 880 mg, preferably about 890 mg, preferably about 900 mg, preferably about 910 mg, preferably about 920 mg, preferably about 930 mg, preferably about 940 mg, preferably about 950 mg, preferably about 960 mg, preferably about 970 mg, preferably about 980 mg, preferably about 990 mg, or more preferably about 1000 mg of the CBD in a single dose.

In an embodiment, the composition comprises a concentration of the volatile anaesthetic in a total amount by weight of from about 1% to about 99.9%, preferably from about 2% to about 99.9%, preferably from about 3% to about 99.9%, preferably from about 4% to about 99.9%, preferably from about 5% to about 99.9%, preferably from about 6% to about 99.9%, preferably from about 7% to about 99.9%, preferably from about 8% to about 99.9%, preferably from about 9% to about 99.9%, preferably from about 10% to about 99.9%, preferably from about 11% to about 99.9%, preferably from about 12% to about 99.9%, preferably from about 13% to about 99.9%, preferably from about 14% to about 99.9%, preferably from about 15% to about 99.9%, preferably from about 16% to about 99.9%, preferably from about 17% to about 99.9%, preferably from about 18% to about 99.9%, preferably from about 19% to about 99.9%, preferably from about 20% to about 99.9%, preferably from about 21% to about 99.9%, preferably from about 22% to about 99.9%, preferably from about 23% to about 99.9%, preferably from about 24% to about 99.9%, preferably from about 25% to about 99.9%, preferably from about 26% to about 99.9%, preferably from about 27% to about 99.9%, preferably from about 28% to about 99.9%, preferably from about 29% to about 99.9%, preferably from about 30% to about 99.9%, preferably from about 31% to about 99.9%, preferably from about 32% to about 99.9%, preferably from about 33% to about 99.9%, preferably from about 34% to about 99.9%, preferably from about 35% to about 99.9%, preferably from about 36% to about 99.9%, preferably from about 37% to about 99.9%, preferably from about 38% to about 99.9%, preferably from about 39% to about 99.9%, preferably from about 40% to about 99.9%, preferably from about 41% to about 99.9%, preferably from about 42% to about 99.9%, preferably from about 43% to about 99.9%, preferably from about 44% to about 99.9%, preferably from about 45% to about 99.9%, preferably from about 46% to about 99.9%, preferably from about 47% to about 99.9%, preferably from about 48% to about 99.9%, preferably from about 49% to about 99.9%, preferably from about 50% to about 99.9%, preferably from about 51% to about 99.9%, preferably from about 52% to about 99.9%, preferably from about 53% to about 99.9%, preferably from about 54% to about 99.9%, preferably from about 55% to about 99.9%, preferably from about 56% to about 99.9%, preferably from about 57% to about 99.9%, preferably from about 58% to about 99.9%, preferably from about 59% to about 99.9%, preferably from about 60% to about 99.9%, preferably from about 61% to about 99.9%, preferably from about 62% to about 99.9%, preferably from about 63% to about 99.9%, preferably from about 64% to about 99.9%, preferably from about 65% to about 99.9%, preferably from about 66% to about 99.9%, preferably from about 67% to about 99.9%, preferably from about 68% to about 99.9%, preferably from about 69% to about 99.9%, preferably from about 70% to about 99.9%, preferably from about 71% to about 99.9%, preferably from about 72% to about 99.9%, preferably from about 73% to about 99.9%, preferably from about 74% to about 99.9%, preferably from about 75% to about 99.9%, preferably from about 76% to about 99.9%, preferably from about 77% to about 99.9%, preferably from about 78% to about 99.9%, preferably from about 79% to about 99.9%, preferably from about 80% to about 99.9%, preferably from about 81% to about 99.9%, preferably from about 82% to about 99.9%, preferably from about 83% to about 99.9%, preferably from about 84% to about 99.9%, preferably from about 85% to about 99.9%, preferably from about 86% to about 99.9%, preferably from about 87% to about 99.9%, preferably from about 88% to about 99.9%, preferably from about 89% to about 99.9%, preferably from about 90% to about 99.9%, preferably from about 91% to about 99.9%, preferably from about 92% to about 99.9%, preferably from about 93% to about 99.9%, preferably from about 94% to about 99.9%, preferably from about 95% to about 99.9%, preferably from about 96% to about 99.9%, preferably from about 97% to about 99.9%, preferably from about 98% to about 99.9%, preferably from about 99% to about 99.9%, preferably from about 99.1% to about 99.9%, preferably from about 99.2% to about 99.9%, preferably from about 99.3% to about 99.9%, preferably from about 99.4% to about 99.9%, preferably from about 99.5% to about 99.9%, preferably from about 99.6% to about 99.9%, preferably from about 99.7% to about 99.9%, or preferably from about 99.8% to about 99.9%.

In an embodiment, the composition is formulated to administer the volatile anaesthetic in an amount effective to target a MAC of from about 0.01 to about 10 (e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10) in a single dose. Thus, in an embodiment, the composition comprises an amount of the volatile anaesthetic effective to target a MAC of about 0.01, preferably about 0.02, preferably about 0.03, preferably about 0.04, preferably about 0.05, preferably about 0.06, preferably about 0.07, preferably about 0.08, preferably about 0.09, preferably about 0.1, preferably about 0.2, preferably about 0.3, preferably about 0.4, preferably about 0.5, preferably about 0.6, preferably about 0.7, preferably about 0.8, preferably about 0.9, preferably about 1, preferably about 1.5, preferably about 2, preferably about 2.5, preferably about 3, preferably about 3.5, preferably about 4, preferably about 4.5, preferably about 5, preferably about 5.5, preferably about 6, preferably about 6.5, preferably about 7, preferably about 7.5, preferably about 8, preferably about 8.5, preferably about 9, preferably about 9.5 or more preferably about 10 in a single dose.

The compositions described herein may additionally include any suitable additives, carriers, additional therapeutic agents, bioavailability enhancers, side-effect suppressing components, diluents, buffers, flavouring agents, binders, preservatives or other ingredients that are not detrimental to the efficacy of the composition.

In an embodiment, the composition further comprises one or more pharmaceutically acceptable carriers, diluents and excipients.

In another embodiment, the composition further comprises one or more additional therapeutic agents. Suitable additional therapeutic agents would be known to persons skilled in the art, illustrative examples of which include anti-anxiety agents, anti-coagulants, anti-convulsants, anti-depressants, muscle relaxants and stimulants.

In an embodiment, the composition further comprises one or more cannabinoids selected from the group consisting of CBG, CBN, CBDL, CBC and THC.

Compositions disclosed herein may be prepared according to conventional methods well known in the pharmaceutical and nutraceutical industries, such as those described in Remington's Pharmaceutical Handbook (Mack Publishing Co., NY, USA) using suitable excipients, diluents and fillers. Exemplary additional ingredients include at least one emulsifier (e.g., polyethylene glycol 400 (PEG-400), propylene glycol, vegetable glycol), butylated hydroxytoluene (E321) etc. In general, compositions formulated for administration by inhalation are delivered by MDIs, DPIs, nebuliser solutions, vaporiser solutions, suspensions and nasal sprays (e.g., aqueous, powder and propellant driven).

Compositions, e.g., compositions suitable for administration by inhalation, may be presented as discrete units (i.e., dosage forms), each containing a predetermined amount of each component of the composition as a powder, granules, as a solution or a suspension in an aqueous liquid or non-aqueous liquid, or as an emulsion.

As described elsewhere herein, the compositions may be formulated for administration as separate unit dosage forms for administration. The unit dosage form may be suitable for an inhaler, a nebuliser, an atomiser, an MDI or a vaporiser.

Those skilled in the art will appreciate that the invention described herein is susceptible to variations and modifications other than those specifically described. It is to be understood that the invention includes all such variations and modifications, which fall within the spirit and scope. The invention also includes all of the steps, features, compositions and compounds referred to or indicated in this specification, individually or collectively, and any and all combinations of any two or more of said steps or features.

Unless otherwise defined, all technical and scientific terms used herein have the same meanings as commonly understood by one of ordinary skill in the art to which this invention belongs.

All patents, patent applications and publications mentioned herein are hereby incorporated by reference in their entireties.

The various embodiments enabled herein are further described by the following non-limiting examples.

EXAMPLES

Example 1—Exemplary Composition for the Treatment of TBI

Exemplary compositions according to the present disclosure have the following ingredients:

Active Ingredients

Synthetic CBD: 20 mg

Methoxyflurane: 3 mL of 1:500 to target a Minimum Alveolar Concentration (MAC) of 0.3

Optional Additional Excipients

Emulsifier

Butylated hydroxytoluene (E321)

Example 2—Exemplary Methods for the Treatment of TBI

An exemplary method for the treatment of TBI according to the present disclosure is as follows:

Composition of Example 1: administration of liquid vaporisable composition to the subject immediately after (i.e., within 30 minutes) after moderate to severe head injury via inhalation.

CBD is highly lipid-soluble and permeates central nervous system (CNS) tissues fast to achieve significant concentrations within two minutes of inhalation. Methoxyflurane is similarly a highly lipid-soluble, volatile anaesthetic that can achieve significant CNS concentrations within 2 minutes of inhalation.

Example 3—CBD and a Volatile Anaesthetic for the Treatment of TBI In Vivo

Materials and Methods

Model Establishment

The effect of cannabidiol (CBD) combined with isoflurane therapy was assessed using a rat model of TBI induced by controlled cortical impact (CCI). Briefly, Sprague-Dawley (SD) rats were anaesthetised with 3% pentobarbital sodium before fixing the head in a stereotaxic frame. After performing a craniotomy, a contusion injury (CCI) was induced with an IMP-3000 TBI Impactor with a diameter of 5.0 mm, a depth of 2.5 mm, dwell time of 100 ms and velocity of 5 m/s. Control rats underwent the same surgical procedure, including craniotomy, without CCI.

Grouping and Treatment

Animals were assigned to treatment groups by randomisation to achieve similar group mean weight. The randomised groups are detailed in Table 2.

TABLE 2

Grouping of animals for in vivo analysis of combination therapy

| | Animal # | | | | | | |
|---|---|---|---|---|---|---|---|
| Group | Male | Female | Model | Treatment | Dosage | Route | Freq. |
| 1 | 6 | 6 | Sham | NA | NA | NA | NA |
| 2 | 6 | 6 | CCI | Placebo 1* | NA | I.P | LD at 15-30 min post-injury; MD × 6 |
| | | | | Placebo 2# | NA | Inhaled | LD at 1 hr post-injury |
| 3 | 6 | 6 | CCI | CBD | 20 mg/kg | I.P | LD at 15-30 min post-injury; MD × 6 |
| | | | | Placebo 2 | NA | Inhaled | LD at 1 hr post-injury |
| 4 | 6 | 6 | CCI | Placebo 1 | NA | I.P | LD at 15-30 min post-injury; MD × 6 |
| | | | | Isoflurane | 1.5% | Inhaled | LD at 1 hr post-injury |
| 5 | 6 | 6 | CCI | CBD | 20 mg/kg | I.P | LD at 15-30 min post-injury; MD × 6 |
| | | | | Isoflurane | 1.5% | Inhaled | LD at 1 hr post-injury |
| 6 | 6 | 6 | CCI | CBD | 20 mg/kg | I.P | LD at 15-30 min post-injury |
| | | | | Isoflurane | 1.5% | Inhaled | LD at 1 hr post-injury |

*Placebo 1: Vehicle (1:1:18 ethanol: Tween 80: saline); #Placebo 2: Air; I.P: Intraperitoneal injection; LD: Loading dose; MD: Maintenance dose.

Behavioural Tests

Behavioural outcomes following CCI were assessed using the Morris Water Maze (MWM), which assesses cognitive defects after CCI injury (see, e.g., Nunez, 2008, *Journal of Visualized Experiments,* 897) and the Rotarod test, which assesses changes in motor function (see, e.g., Shiotsuki et al., 2010, *Journal of Neuroscience Methods,* 189: 180-185).

Results

The combinatorial neuroprotective effects of CBD and isoflurane were assessed using a rat controlled cortical impact model of TBI. Briefly, head injury is induced in the rats by first performing a craniotomy to remove a small disc of bone from the skull and then using a pneumatic rod to directly impact the exposed brain. Controlled Cortical Impact (CCI) parameters used in this study were 2.5 mm depth, 5 m/s velocity, 100 ms dwell time. Sham control animals underwent an identical surgical procedure, including craniotomy, but without the CCI injury.

Animals were treated with CBD (20 mg/kg) and isoflurane (1.5%) both alone and in combination (Table 2). A loading dose comprising CBD and isoflurane was administered sequentially, with CBD administered 15-30 min post injury and isoflurane administered 1-2 h after injury. Daily maintenance doses of CBD were administered for six consecutive days after administration of the loading dose.

To determine the neuroprotective effects associated with the combination of CBD and isoflurane, the MWM, a well-established assay for investigation of spatial learning and memory (Nunez, 2008, supra; D'Hooge et al., 2001, *Brain Research Reviews,* 36: 60-90), and the Rotarod, a device used to monitor motor coordination (Deacon, 2013, *Journal of Visualized Expreiments, e*2609-e2609; Shitosuki et al., 2010, supra), were used 7-days post-head injury. The predicted combinatorial effects of CBD and isoflurane were calculated using the Bliss independence principle using the equation:

$$E_{pred\ A+B}=(E_A+E_B)-(E_AE_B)$$

The activity of the combination for this equation was calculated as:

$$(X\text{-placebo})/(\text{sham}-\text{placebo})$$

Synergy between two agents occurs when the difference between the observed activity of the agents in combination is greater than the predicted activity. Based on these measures, the combination of CBD and isoflurane synergize to improve spatial learning and memory and motor coordination in vivo.

In the MWM a rat is trained to recognise where a platform is located in a water tank over a series of days. It is then released into the tank and monitored for the ability to locate the platform. A lack of ability to locate the platform is indicative of a spatial memory neurocognitive deficit. The combination of CBD and isoflurane had a synergistic effect on improving spatial memory with respect to both instances of the rat being located at the platform (Table 3) and the number of rats who successfully located the platform (Table 4).

TABLE 3

| MWM: number of instances of rats reaching the platform | | |
|---|---|---|
| Treatment | Instances of centre of rat corresponding to platform location normalised to the number of rats in group | E (normalised activity value used to calculate synergy) |
| Sham | 1 | 1 |
| Placebo | 0.5 | 0 |

TABLE 3-continued

| MWM: number of instances of rats reaching the platform | | |
|---|---|---|
| Treatment | Instances of centre of rat corresponding to platform location normalised to the number of rats in group | E (normalised activity value used to calculate synergy) |
| 20 mg/kg CBD | 0.4 | −0.2 |
| 1.5% isoflurane | 0.83 | 0.67 |
| Predicted combination effect | 0.8 | 0.60 |
| Observed combination effect | 1.5 | 2 |
| Observed-Predicted effect. | 0.7 | 1.4 |

TABLE 4

| MWM: proportion of rats that reached the platform | | |
|---|---|---|
| Treatment | Number of rats that reached the platform normalised to the total number of rats in each group | E (normalised activity value used to calculate synergy) |
| Sham | 0.67 | 1.0 |
| Placebo | 0.33 | 0 |
| 20 mg/kg CBD | 0.4 | 0.21 |
| 1.5% isoflurane | 0.5 | 0.50 |
| Predicted combination effect | 0.54 | 0.54 |
| Observed combination effect | 0.67 | 1.0 |
| Observed-Predicted effect. | 0.13 | 0.46 |

In the Rotarod assay rats are place on a rotating cylinder and monitored for the time it takes them to fall off, or latency. A shorter latency is indicated of a motor function deficit. CBD and isoflurane had a synergistic effect on increasing latency in rats who had undergone CCI TBI.

TABLE 5

| Rotarod latencies | | |
|---|---|---|
| Treatment | Latency (s) | E (normalised activity value used to calculate synergy) |
| Sham | 23.39 | 1 |
| Placebo | 17.83 | 0 |
| 20 mg/kg CBD | 17.60 | −0.04 |
| 1.5 % isoflurane | 17.33 | −0.09 |
| Predicted combination effect | 17.08 | −0.14 |
| Observed combination effect | 19.33 | 0.27 |
| Observed-Predicted effect. | 2.25 | 0.41 |

To determine whether there was a benefit for treating with CBD for 7 days (i.e., loading dose+6 consecutive maintenance doses) compared to loading dose only treatment groups were also included where they received isoflurane at 1.5% as well as CBD at 20 mg/kg but only on the day of injury. While administration of the loading dose alone was sufficient to improve the symptoms of TBI, the 7-day treatment led to better performance in both the MWM and Rotarod assays (Table 6).

TABLE 6

| Comparison of loading dose only and loading dose with maintenance dose | | | |
|---|---|---|---|
| Treatment | MWM instances of platform finding | MWM proportion of rats finding platform | Rotarod latency (s) |
| Isoflurane CBD LD + MD | 1.50 | 0.67 | 19.33 |
| Isoflurane CBD LD | 0.83 | 0.67 | 16.78 |

CONCLUSION

The data presented herein demonstrate that the combination of CBD and a volatile anaesthetic, e.g., isoflurane, synergize to effectively treat or prevent the development of symptoms of TBI following a head injury.

The administration of a single loading dose of CBD and a volatile anaesthetic is sufficient to improve spatial memory and motor function in an established in vivo model of TBI. The improvement in motor function observed following the administration of a single loading dose of CBD and a volatile anaesthetic was further improved where six consecutive maintenance doses of CBD was administered following the initial loading dose. Taken together, these data are enabling of methods for the treatment or prevention of TBI and compositions comprising CBD and a volatile anaesthetic.

BIBLIOGRAPHY

Blair and Frampton, 2016, *Clinical Drug Investigation,* 36(12): 1067-1073;

Deacon, 2013, *Journal of Visualized Expreiments, e*2609-e2609;

D'Hooge et al., 2001, *Brain Research Reviews,* 36: 60-90;

Ghelichkhani et al., 2018, *Emergency* (*Tehran*), 6(1): e42;

Jain et al., 2010, *Journal of Cerebral Blood Flow & Metabolism,* 30(9): 1598-1607;

Nunez, 2008, *Journal of Visualized Experiments,* 897;

Rahn and Hohmann, 2009, *Neurotherapeutics* 6:713-37;

Sanchez and Verpoote, 2008, *Plant and Cell Physiology,* 49(12): 1767-82;

Shiotsuki et al., 2010, *Journal of Neuroscience Methods,* 189: 180-185;

Solowij et al., 2014, *BMC Pharmacology and Toxicology,* 15;

U.S. Pat. No. 10,189,762;

WO 2004/016277; and

WO 2016/001922.

The claims defining the invention are as follows:

1. A method for the treatment of traumatic brain injury (TBI) comprising administering to a subject in need thereof a loading dose comprising an effective amount of cannabidiol (CBD), or a pharmaceutically acceptable salt thereof, and a volatile anaesthetic, wherein the volatile anaesthetic is isoflurane.

2. The method of claim 1, further comprising administering one or more maintenance dose(s) of the CBD, wherein the maintenance dose of the CBD is administered subsequent to the administration of the loading dose.

3. The method of claim 2, wherein the maintenance dose of the CBD is administered at least one day after the administration of the loading dose.

4. The method of claim 1, wherein the CBD is a synthetic compound.

5. The method of claim 1, wherein the loading dose comprises an amount of the volatile anaesthetic effective to target a Minimum Alveolar Concentration (MAC) of from about 0.01 to about 10.

6. The method of claim 1, wherein the loading dose comprises from about 0.1 mg to about 1000 mg of CBD.

7. The method of claim 2, wherein the maintenance dose comprises from about 0.1 mg to about 1000 mg of CBD.

8. The method of claim 1, wherein the loading dose of CBD is administered to the subject by a method selected from the group consisting of inhalation, oral administration, nasal administration and parenteral administration.

9. The method of claim 8, wherein the loading dose of CBD is administered to the subject by inhalation.

10. The method of claim 1, wherein the TBI is mild TBI.

11. The method of claim 1, wherein the TBI is acute brain injury.

12. The method of claim 1, wherein the loading dose is administered from about 10 minutes to about 24 hours after a head injury has occurred.

13. The method of claim 1, wherein the loading dose of the CBD and the volatile anaesthetic are administered simultaneously.

14. The method of claim 1, wherein the loading dose of the CBD and the volatile anaesthetic are administered sequentially.

15. The method of claim 1, further comprising the administration of one or more cannabinoids selected from the group consisting of cannabigerol (CBG), cannabinol (CBN), cannabinodiol (CBDL), cannabichromene (CBC) and delta-9-tetrahydrocannabinol (THC).

16. A method for the treatment of TBI comprising administering to a subject in need thereof an effective amount of a composition comprising CBD, or a pharmaceutically acceptable salt thereof, and a volatile anaesthetic, wherein the volatile anaesthetic is isoflurane.

17. The method of claim 16, wherein the CBD is a synthetic compound.

18. The method of claim 16, wherein the composition comprises one or more or all of:

a. the volatile anaesthetic in an amount effective to target a MAC of from about 0.01 to about 10 in a single dose;

b. from about 0.1 mg to about 1000 mg of the CBD in a single dose;

c. one or more pharmaceutically acceptable carriers, diluents and excipients; and d. one or more cannabinoids selected from the group consisting of CBG, CBN, CBDL, CBC and THC.

19. The method of claim 16, wherein the composition is for administration by inhalation.

20. The method of claim 1, wherein the TBI is moderate TBI.

21. The method of claim 1, wherein the TBI is severe TBI.

* * * * *